United States Patent
Olasz et al.

(10) Patent No.: US 8,367,394 B2
(45) Date of Patent: Feb. 5, 2013

(54) PROCESS FOR THE SYNTHESIS OF 9α-HYDROXY-STEROIDS

(75) Inventors: Katalin Olasz, Budapest (HU); Anikó Tegdes, Budapest (HU); Valéria Gancsos, Dombrad (HU); Gábor Hantos, Budapest (HU); Kálmán Könczöl, Budapest (HU); Gabor Balogh, Budapest (HU); Sándor Erdélyi, Tápióság (HU)

(73) Assignee: Richter Gedeon Nyrt., Budapest (HU)

( * ) Notice: Subject to any disclaimer, the term of this patent is extended or adjusted under 35 U.S.C. 154(b) by 405 days.

(21) Appl. No.: 12/665,351

(22) PCT Filed: Jun. 30, 2008

(86) PCT No.: PCT/HU2008/000078
§ 371 (c)(1),
(2), (4) Date: Apr. 14, 2010

(87) PCT Pub. No.: WO2009/004394
PCT Pub. Date: Jan. 8, 2009

(65) Prior Publication Data
US 2010/0209967 A1  Aug. 19, 2010

(30) Foreign Application Priority Data
Jul. 4, 2007  (HU) .................... 0700461

(51) Int. Cl.
*C12P 33/20* (2006.01)
*C12N 1/21* (2006.01)
*C12P 1/00* (2006.01)
*C12P 33/00* (2006.01)
*C12N 1/00* (2006.01)
*C12N 1/20* (2006.01)

(52) U.S. Cl. ........... 435/253.2; 435/53; 435/41; 435/52; 435/243; 435/252.1

(58) Field of Classification Search .................. None
See application file for complete search history.

(56) References Cited

U.S. PATENT DOCUMENTS
4,397,947 A   8/1983  Marshek et al. ............. 435/58
6,331,622 B1  12/2001  Ng et al. ...................... 540/41

OTHER PUBLICATIONS

Preisig et al: "Biotransformations of the cardiovascular drugs mextrenone and canrenone", Journal of Natural products, vol. 6, No. 3, 2003, pp. 350-356.
Datcheva et al: "Synthesis of 9alpha-hydroxysteroids by a *Rhodococcus* sp", Steroids, Elsevier Science Publishers, New York, vol. 54, No. 3 (1989), p. 278, table 1.

*Primary Examiner* — Chris R Tate
*Assistant Examiner* — Aaron J Kosar
(74) *Attorney, Agent, or Firm* — Jonathan Myers; Andrew Wilford

(57) ABSTRACT

The present invention relates to a novel selective synthesis of 9α-hydroxy-steroid derivatives of the general formula (I) (I)—wherein the meaning of -A-A'- is —$CH_2$—$CH_2$— or —CH=CH— group—by the bioconversion of compounds of the general formula (II) (II) wherein the meaning of -A-A'- is —$CH_2$—$CH_2$— or —CH=CH— group—by using *Nocardia farcinica* bacterium strain, deposition number of which is NCAIM (P)—B 001342, as hydroxylating microorganism in the bioconversion.

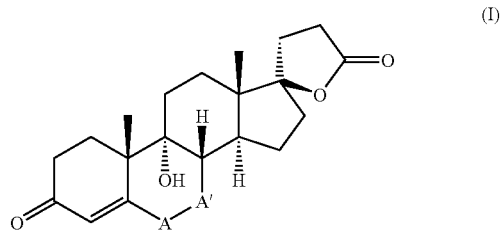

(I)

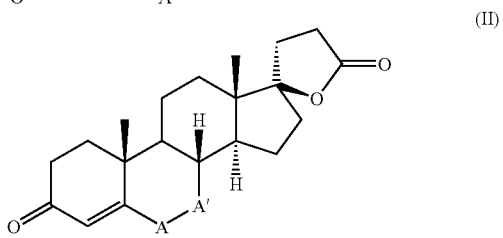

(II)

7 Claims, 1 Drawing Sheet

SEQUENCE LISTING

```
<160> NUMBER OF SEQ ID NOS: 1

<210> SEQ ID NO 1
<211> LENGTH: 1369
<212> TYPE: DNA
<213> ORGANISM: Nocardia sp. Fla (RG 4451)

<400> SEQUENCE: 1
gtcgagcggt aaggcccttc ggggtacacg agcggcgaac gggtgagtaa cacgtgggtg      60
atctgccctg tacttcggga taagcctggg aaactgggtc taataccgga tatgacctta     120
catcgcatgg tgtttggtgg aaagatttat cggtacagga tgggcccgcg gcctatcagc     180
ttgttggtgg ggtaatggcc taccaaggcg acgacgggta gccggcctga gagggcgacc     240
ggccacactg ggactgagac acggcccaga ctcctacggg aggcagcagt ggggaatatt     300
gcacaatggg cgaaagcctg atgcagcgac gccgcgtgag ggatgacggc cttcgggttg     360
taaacctctt tcgacaggga cgaagcgcaa gtgacggtac ctgtagaaga agcaccggcc     420
aactacgtgc cagcagccgc ggtaatacgt agggtgcgag cgttgtccgg aattactggg     480
cgtaaagagc ttgtaggcgg tttgtcgcgt cgtccgtgaa aacttgggc tcaaccccaa      540 gcttgcgggc gatacgggca gacttgagta ctgcaggga gactggaatt cctggtgtag     600
cggtgaaatg cgcagatatc aggaggaaca ccggtggcga aggcgggtct ctgggcagta     660
```

```
actgacgctg agaagcgaaa gcgtgggtag cgaacaggat tagataccct ggtagtccac    720
gccgtaaacg gtgggcgcta ggtgtgggtt tccttccacg ggatccgtgc cgtagctaac    780
gcattaagcg ccccgcctgg ggagtacggc cgcaaggcta aaactcaaag gaattgacgg    840
gggcccgcac aagcggcgga gcatgtggat taattcgatg caacgcgaag aaccttacct    900
gggtttgaca tacaccggaa acctgcagag atgtaggccc ccttgtggtc ggtgtacagg    960
tggtgcatgg ctgtcgtcag ctcgtgtcgt gagatgttgg gttaagtccc gcaacgagcg   1020 caaccccttgt cctgtgttgc cagcgcgtta tggcggggac tcgcaggaga ctgccggggt   1080
caactcggag gaaggtgggg acgacgtcaa gtcatcatgc cccttatgtc cagggcttca   1140
cacatgctac aatggccggt acagagggct gcgataccgt gaggtggagc gaatccctta   1200
aagccggtct cagttcggat cggggtctgc aactcgaccc cgtgaagttg gagtcgctag   1260
taatcgcaga tcagcaacgc tgcggtgaat acgttcccgg gccttgtaca caccgcccgt   1320
cacgtcatga aagtcggtaa cacccgaagc cggtggccta accccttgt              1369
```

PROCESS FOR THE SYNTHESIS OF 9α-HYDROXY-STEROIDS

CROSS REFERENCE TO RELATED APPLICATIONS

This application is the US national phase of PCT application PCT/HU2008/000078, filed 30 Jun. 2008, published 8 Jan. 2009 as WO2009/004394, and claiming the priority of Hungarian patent application P0700461 itself filed 4 Jul. 2007, whose entire disclosures are herewith incorporated by reference.

FIELD OF THE INVENTION

The present invention relates to a novel selective synthesis of 9α-hydroxy-steroid derivatives of the formula

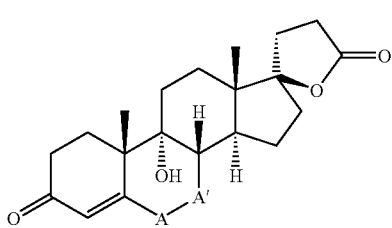

(I)

wherein the meaning of -A-A'- is —$CH_2$—$CH_2$— or —CH=CH— group—by the bioconversion of compounds of the formula (II)

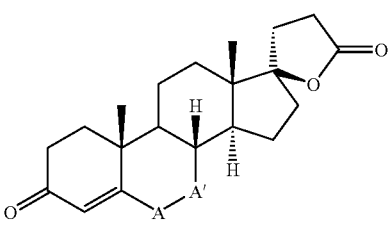

(II)

wherein the meaning of -A-A'- is —$CH_2$—$CH_2$— or —CH=CH— group.

BACKGROUND OF THE INVENTION

It is known that 9α-hydroxy-steroids are widely used in therapy, as for example the 9α-hydroxy derivatives of pregnane steroids have glucocorticoid activity as well as the 9α-hydroxy derivatives of androstane derivatives are used as active ingredients of anti-androgen and anti-estrogen drugs.

Those 9α-hydroxy-steroids which do not have substituent in position 11 can easily be dehydrated by known chemical methods and the so obtained 9(11)-dehydro-steroids are important intermediates in the synthesis of compounds possessing high biological activity. Such compounds are for example hydrocortisone (chemical name: 11β,17,21-trihydroxy-pregn-4-ene-3,20-dione) and prednisolone (chemical name: 11β,17,21-trihydroxy-pregn-1,4-diene-3,20-dione) having anti-inflammatory activity or eplerenone (chemical name: 9α,11α-epoxy-17β-hydroxy-3-oxo-pregna-4-ene-7,21-dicarboxylic acid gamma lactone) the latter having abroad indication profile; for example it decreases the risk of mortality caused by heart and blood-vessel problems similarly to beta-blockers and it is also used for the treatment of high blood pressure and as a diuretic.

The members of the $\Delta^4$-3-keto-pregnane family were first hydroxylated in the 9α-position by Hanze and coworkers in 1958 using Cunninghamella and Helicostylum thread fungus strains (see: U.S. Pat. No. 3,038,913). In 1960 Sih and coworkers described the 9α-hydroxylation of steroids using microorganisms having $\Delta^1$-dehydrogenase enzyme activity in the presence of $\Delta^1$-dehydrogenase inhibitor (see: U.S. Pat. No. 3,065,146). Two years later Sebek carried out the 9α-hydroxylation of steroids by using Ascochyta linecola strain (see: U.S. Pat. No. 3,116,220).

In the previously mentioned patent Sih and coworkers also listed mycobacteria strains as microorganisms having steroid 9α-hydroxylase enzymes (see: U.S. Pat. No. 3,065,146).

It is known, that in 1977 Frederick and coworkers produced a new mycobacterium strain by mutagenic treatment, which only partially degraded the examined sterol substrates and therefore the 9α-hydroxy derivatives were accumulated (see: U.S. Pat. No. 4,029,549). Wovcha used the same strain—Mycobacterium fortuitum NRRL B-8119 strain—for the synthesis of new 9α-hydroxy derivatives (see: U.S. Pat. No. 4,035,236).

Wovcha and coworkers studied the role of Mycobacterium fortuitum ATCC 6842 strain in the degradation of the steroid backbone. They found that the key step in the degradation into carbon dioxide and water is the subsequent functioning of $\Delta^1$-dehydrogenase and 9α-hydroxylase enzymes. The two conversion steps can be interchanged that is both reaction steps can be carried out by two-two enzymes (group of enzymes); for example one of them, the $\Delta^1$-dehydrogenase enzyme converts the starting material and the other $\Delta^1$-dehydrogenate the 9α-hydroxy derivative. In their experiments they supposed, that the above enzymes can be induced; and by using different inducers the amount and the composition of the formed products varied significantly [Biochimica et Biophysica Acta 574, 471-479 (1979)].

In 1981 Marsheck and coworkers carried out the 9α-hydroxylation of steroid compounds by using a new mutant Nocardia canicruria strain in such a way that it was not necessary to use $\Delta^1$-dehydrogenase enzyme inhibitor. In the above mentioned examples the synthesis of 9α-hydroxy-ketolactone (chemical name: 9α,17-dihydroxy-3-oxo-17α-pregna-4-ene-21-carboxylic acid gamma lactone) is described starting from ketolactone (chemical name: 17-hydroxy-3-oxo-17a-pregna-4-ene-21-carboxylic acid gamma lactone); using 0.5 g/dm³ concentration of the ketolactone substrate the desired hydroxylated product was formed in 30% conversion (see: U.S. Pat. No. 4,397,947).

Among others Mutafov and coworkers studied the inducibility of the steroid 9α-hydroxylase enzyme using Rhodococcus sp. strain and found that 9α-hydroxy-4-androstene-3,17-dione formed as a product was a very poor inducer, since using it as an inducer slowed the reaction rate in half and the amount of the formed 9α-hydroxy product was a quarter of that when 4-androstene-3,17-dione was used as inducer [Process Biochemistry 32 (7), 585-589 (1997)].

Brzostek and coworkers studied the degradation of the steroid backbone on gene level and found that blocking the $\Delta^1$-dehydrogenase enzyme activity, which is needed for the synthesis 9α-hydroxy steroid derivatives, is difficult, because there are not only different types of $\Delta^1$-dehydrogenase enzymes but the genome contains in some cases five $\Delta^1$-dehydrogenase genes [Microbiology 151, 2393-2402 (2005)].

It is known that a microbiological step is carried out besides the chemical reaction steps in the synthesis of eplerenone, among others the hydroxylation of a valuable intermediate, the canrenone (chemical name: 17-hydroxy-3-oxo-17α-pregna-4,6-diene-21-carboxylic acid gamma lactone), was carried out with microorganisms (*Diplodia, Aspergillus, Absidia* sp.) (see: US Patent Applications No. 2004/087562 and 2004/097475 and further PCT International Patent Application No 2005/000865).

Another synthesis of eplerenone can be carried out via 9α-hydroxylation of canrenone. The 9α-hydroxy-canrenone (chemical name: 9α,17-dihydroxy-3-oxo-17α-pregna-4,6-diene-21-carboxylic acid gamma lactone) was first synthesized by Ng and coworkers by microbiological hydroxylation (see: PCT International Patent Appl. No 97/21720 and Hungarian patent No 222,453) and described in Example 17 in the above mentioned patents.

The 9α-hydroxy-canrenone as product is first described in patent claims in 1998 in the patent of Ng and coworkers (see: PCT International Patent Appl. No 98/25948; or later U.S. Pat. No. 7,129,345).

The international search examining authority found 18 independent inventions in the PCT-patent applications No 97/21720 and 98/25948, therefore they suggested to the inventor to file selection patent applications. As a result of this more than 100 patent applications were filed, from which several contains Example 17 of the above mentioned patent No. WO-97/21720 (see PCT No 2005/239761).

The above mentioned Example 17 describes the screening data of 83 microorganisms, which potentially have steroid 9α-hydroxylating enzyme activity and gives the TLC, HPLC/UV and LC/MS data of the products formed during the bioconversion of canrenone. From the table given there it can only be seen that the 9α-hydroxy-canrenone can be detected by the above mentioned analytical methods in the possible products or not. There is a mycobacterium in this table, *Mycobacterium fortuitum* ATCC 6842 strain, but there are no analytical data given in the appropriate columns. The bioconversion ability of this strain is known from the literature [publications starting from 1936, Acta Med. Rio de Janeiro 1,1], therefore it can be supposed that decomposition of canrenone took place (see U.S. Pat. Nos. 4,029,549 and 4,035,236).

This presumption is supported by a publication, which was written in 2003 by the microbiologist inventors of the above mentioned patent family. This publication contains the same table, but the *Mycobacterium fortuitum* strain in this table a variant of the above, developed for 9α-hydroxylation of steroids: registry number NRRL B-8119 [J. Nat. Prod. 66, 350-356 (2003)]. In this case according to the authors the *Mycobacterium fortuitum* NRRL B-8119 did not produce hydroxy or dehydrogenated product and there was no metabolism.

In the above mentioned Example 17 there are 3 types of *Nocardia* strains, namely: *Nocardia aurentis, Nocardia cancicruria* and *Nocardia coralline* strains. According to TLC and HPLC measurements the conversion products of two strains are similar to 9α-hydroxy-canrenone, but the formation of 9α-hydroxy-canrenone was disclosed by LC/MS analysis.

The only microbiological synthesis of 9α-hydroxy-canrenone in which numerical data are given is described in the above mentioned publication: *Corynespora cassiicola* ATCC 16718 strain was used in aerobic fermentation carried out in a flask, using 0.1 g/dm³ concentration of canrenone substrate the desired hydroxylated product was formed in 30% conversion [J. Nat. Prod. 66, 350-356 (2003)].

As it can be seen from above mentioned publications there is no such microbiological synthesis of 9α-hydroxy derivatives of canrenone or ketolactone, which is industrially applicable.

The aim of our invention is therefore to elaborate an industrially applicable microbiological process for the hydroxylation of steroid of the formula (II), wherein the meaning of -A-A'- is —$CH_2$—$CH_2$— or —CH═CH— group, as substrate in position 9 without considerable degradation and by-product formation.

In our initial experiments mycobacterium strains proved to be the most suitable for the microbiological synthesis of 9α-hydroxy-canrenone. The conversion ability of 38 mycobacterium and *Nocardia* strains were screened using ketolactone and canrenone as substrate. Among these strains there were wild type sterol degrading ones, for example *Mycobacterium fortuitum* ATCC 6842, or partially backbone degrading *Mycobacterium fortuitum* NRRL B-8129; as well as several strains, definitely developed for 9α-hydroxylation: *Mycobacterium fortuitum* NRRL B-8119, *Mycobacterium* sp. NCAIM 1072, *Mycobacterium* sp. NCAIM 324.

During the screening we found 3 strains, which—according to TLC analysis—produced detectable amount of 9α-hydroxy derivative: *Mycobacterium fortuitum* NCAIM 00327, *Mycobacterium fortuitum* NCAIM 00323 and *Nocardia* sp. RG 1369.

All of the three strains are able to convert the compound of the formula (II), wherein the meaning of -A-A'- is —$CH_2$—$CH_2$— group, into 9α-hydroxy derivative. However we found, that only *Nocardia* sp. RG 1369 strain is able to convert the compound of the formula (II), wherein the meaning of -A-A'- is —CH═CH— group, into 9α-hydroxy derivative.

In order to improve this conversion ability we carried out experiments in shaken flasks, using glucose, saccharose or glycerol as carbon source, preferably 5-25 g/dm³ glycerol, more preferably 15 g/dm³ glycerol, as well as using yeast extract, plant peptone or malt extract as nitrogen source, preferably using the yeast extract, the plant peptone and the malt extract together in 1-10 g/dm³ concentration, more preferably in 5-5 g/dm³ concentration, in given case applying ammonium, phosphate, potassium, magnesium and iron in their appropriate compounds. The cultivation temperature was 28-35° C., preferably 32° C. When *Nocardia* sp. RG 1369 strain was cultured as mentioned above and the canrenone substrate was added in 4 g/dm³ concentration we found that a significant amount of the steroid decomposed in a few hours, although the 9α-hydroxy-canrenone product can still be isolated, but after 24 hours of the addition of the substrate the total degradation of the steroid backbone was observed.

In our further experiments we tried to shift the reaction towards the formation of 9α-hydroxy-canrenone by using a selective inducer. From among the known inducers AD (chemical name: 4-androstene-3,17-dione) and 10,11-dihydroxy-levodione (chemical name: 13-ethyl-10,11α-dihydroxy-4-gonene-3,17-dione) were active. When 10,11-dihydroxy-levodione was used as an inducer the decomposition took place 6-10 hours later, than in the case of AD. The 10,11-dihydroxy-levodione inducer was dissolved in a mixture of methanol-water, preferably in a 3:1 mixture, at elevated temperature, preferably at 50° C. and filtered to obtain a sterile solution. It was added to the culture at the end of the lag period, after 10-24 hours, preferably after 18 hours, in 0.01-0.5 g/dm³ concentration, preferably in 0.05 g/dm³ concentration.

According to our experiments the degradation can be delayed by addition of $\Delta^1$-dehydrogenase enzyme inhibitors such as chloramphenicol, oxytetracycline and streptomycin antibiotics as well as quinones, for example hydroquinone, naphthoquinone and ninhydrin. We obtained the best results when we used streptomycin; the decomposition time was 3-7 hours longer. In our experiments the antibiotic was added 2-8 hours after the induction, preferably after 6 hours, in 2-10 mg/dm$^3$, preferably in 6 mg/dm$^3$ final concentration.

After analyzing the results of our experiments we recognized that we have to try to produce a strain starting from Nocardia sp. RG 1369 strain by mutagenic treatment and selection, which can be used in the industrial process for the synthesis of the compound of the formula (I), wherein the meaning of -A-A'- is —CH$_2$—CH$_2$— or —CH=CH— group.

From among the possible mutagenic treatments we choose irradiation with UV light of 254 nm wavelength. During the mutagenic treatment the culture of Nocardia sp. RG 1369, which was suspended in physiological saline and kept under aseptic condition, was treated by known method using Mineralight UVGL-58 type lamp from 15 cm for 23 min—the irradiation time was chosen on the basis of the previously measured lethality curve.

The neat cultures, which were obtained by known methods, were screened and surprisingly it was found, that there was one isolate, which was able to convert the compound of the formula (II), wherein the meaning of -A-A'- is —CH$_2$—CH$_2$— or —CH=CH— group, into the compound of the formula (I), wherein the meaning of -A-A'- is —CH$_2$—CH$_2$— or —CH=CH— group, without considerable degradation. The so obtained Nocardia sp. F1a (RG 4451) bacterium mutant was able to perform higher than 80% conversion. Upon rRNA sequencing the bacterium was identified as Nocardia farcinica NCAIM (P)—B 001342 and deposited on 4 Jun. 2007 for the purposes of patent procedure under the Budapest Treaty at the Hungarian National Collection of Agricultural and Industrial Microorganisms (NCAIM), Budapest, Somloi ut, 14-16, 1118, Budapest, Hungary.

According to the above mentioned facts the invention relates to a process for the selective synthesis of compound of the formula (I),

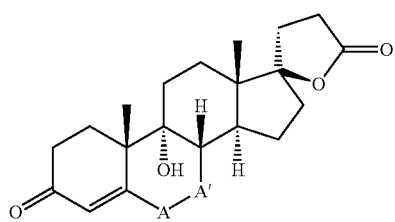

(I)

wherein the meaning of -A-A'- is —CH2-CH2- or —CH=CH— group, by the bioconversion of compound of the formula (II),

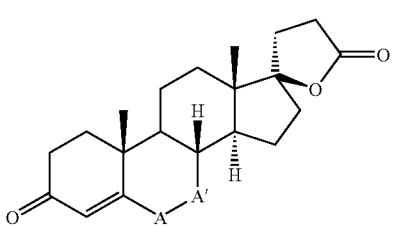

(II)

wherein the meaning of -A-A'- or —CH=CH— group, comprising using Nocardia farcinica bacterium strain, deposition number of which is NCAIM (P)—B 001342, as hydroxylating microorganism in the bioconversion.

The morphological characteristics of the new mutant Nocardia farcinica NCAIM (P)—B 001342 strain show small dissimilarity to those of the starting Nocardia sp. RG 1369 strain. This difference is most visible on the surface of YTA agar (composition of which is: 10 g/dm$^3$ of tripcasein; 1 g/dm$^3$ of yeast extract; 5 g/dm$^3$ of sodium chloride; 0.25 g/dm$^3$ of magnesium sulfate heptahydrate; 0.07 g/dm$^3$ of calcium chloride dihydrate; 20 g/dm$^3$ of agar-agar): the starting Nocardia sp. RG 1369 strain produces yellow-orange pigment and its surface is plain, shiny, most of the developed culture can be found below the surface of the agar and not above it. In contrast to this the surface of cultures of the new mutant Nocardia farcinica NCAIM (P)—B 001342 strain is not plain, but wrinkled and only small portion of them can be found below the surface of the agar.

The identification of the bacterium strain was done by the partial sequence analysis of 16S rRNA gene.
>RG1(Nocardia sp. F1a (RG 4451) fullseqed2, hereinafter SEQ ID NO: 1:

GTCGAGCGGTAAGGCCCTTCGCGGTACACGAGCGGCGAACGGGTGAGTAA

CACGTGGGTGATCTGCCCTGTACTTCGGGATAAGCCTGGGAAACTGGGTC

TAATACCGGATATGACCTTACATCGCATGGTGTTTGGTGGAAAGATTTAT

CGGTACAGGATGGGCCCGCGGCCTATCAGCTTGTTGGTGGGGTAATGGCC

TACCAAGGCGACGACGGGTAGCCGGCCTGAGAGGGCGACCGGCCACACTG

GGACTGAGACACGGCCCAGACTCCTACGGGAGGCAGCAGTGGGGAATATT

GCACAATGGGCGAAAGCCTGATGCAGCGACGCCGCGTGAGGGATGACGGC

CTTCGGGTTGTAAACCTCTTTCGACAGGGACGAAGCGCAAGTGACGGTAC

CTGTAGAAGAAGCACCGGCCAACTACGTGCCAGCAGCCGCGGTAATACGT

AGGCTGCGAGCGTTGTCCGGAATTACTGGGCGTAAAGAGCTTGTAGGCGG

TTTGTCGCGTCGTCCGTCAAAACTTGGGGCTCAACCCCAAGCTTGCGGGC

GATACGGGCAGACTTGAGTACTGCAGGGGAGACTGGAATTCCTGGTGTAG

CGGTGAAATGCGCAGATATCAGGAGGAACACCGGTGGCGAAGGCGGGTCT

CTGGCCAGTAACTGACGCTGAGAAGCGAAAGCGTGGGTAGCGAACAGGAT

TAGATACCCTGGTAGTCCACGCCGTAAACGGTGGGCGCTAGGTGTGGGTT

TCCTTCCACGGGATCCGTGCCGTAGCTAACGCATTAAGCGCCCCGCCTGG

GGAGTACGGCCGCAAGGCTAAAACTCAAAGGAATTGACGGGGGCCCGCAC

AAGCGGCGGAGCATGTGGATTAATTCGATGCAACGCGAAGAACCTTACCT

GGGTTTGACATACACCGGAAACCTGCAGAGATGTAGGCCCCCTTGTGGTC

GGTGTACAGGTGGTGCATGGCTGTCGTCAGCTCGTGTCGTGAGATGTTGC

GTTAACTCCCGCAACGAGCGCAACCCTTGTCCTGTGTTGCCAGCGCGTTA

TGCCGGGGACTCGCAGGAGACTGCCGGGGTCAACTCGGAGGAAGGTGGGG

ACGACGTCAAGTCATCATGCCCCTTATGTCCAGGGCTTCACACATGCTAC

AATGGCCGGTACAGAGGGCTGCGATACCGTGAGGTGGAGCGAATCCCTTA

AAGCCGGTCTCAGTTCGGATCGGGGTCTGCAACTCGACCCCGTGAAGTTG

GAGTCGCTAGTAATCGCAGATCAGCAACGCTGCGGTGAATACGTTCCCGG

CCCTTGTACACACCGCCCGTCACGTCATGAAAGTCGGTAACACCCGAAGC

CGGTGGCCTAACCCCTTGT

The obtained sequence (1396 bp) covers the 91% of the full gene (1527 bp).

The species identification of the studied strain can be determined on the basis of the NCBI BLAST hits by the applied genotaxonomical method: the correct species designation of RG 4451 strain is *Nocardia farcinica*.

Its place in the systematics of the living organisms: *Nocardia farcinica* Trevisan 1889 [3] Cellular organisms; Bacteria; Actinobacteria; Actinobacteria; Actinobacteridae; Actinomycetales; Corynebacterineae; Nocardiaceae; *Nocardia; Nocardia farcinica*

The exact data of the applied NCBI BLAST [2] identification:
Accessibility: (ncbi.nlm.nih.gov/blast/,) Version: BLASTN 2.2.16 (Mar-25-2007)
Database: All GenBank+EMBL+DDBJ+PDB sequences but no EST, STS, GSS, environmental samples or phase 0, 1 or 2 HTGS sequences); 5,284,371 sequences;
20,692,750,832 total letters, Algorithm: megablast The 16S rRNS gene sequence of strains belonging to *Nocardia farcinica* species is identical or very similar to each other. The similarity is also considerable in the subgenus, but the families of Corynebacterineae genus (see Nocardiaceae, Mycobacteriaceae) are very different.

An important and clearly observable difference between the two strains is the conversion ability in synthesizing the compound of the formula (I), wherein the meaning of -A-A'- is —$CH_2$—$CH_2$— or —CH═CH— group, that is the new mutant Nocardia farcinica NCAIM (P)—B 001342 strain retained the 9α-hydroxylation ability, but the degradation of the steroid backbone is suppressed. Therefore—under the previously defined experimental conditions—due to the suppressed degradation the amount of the 9α-hydroxy product is higher, it can be isolated: it can be used on industrial scale synthesis.

Figure 1:
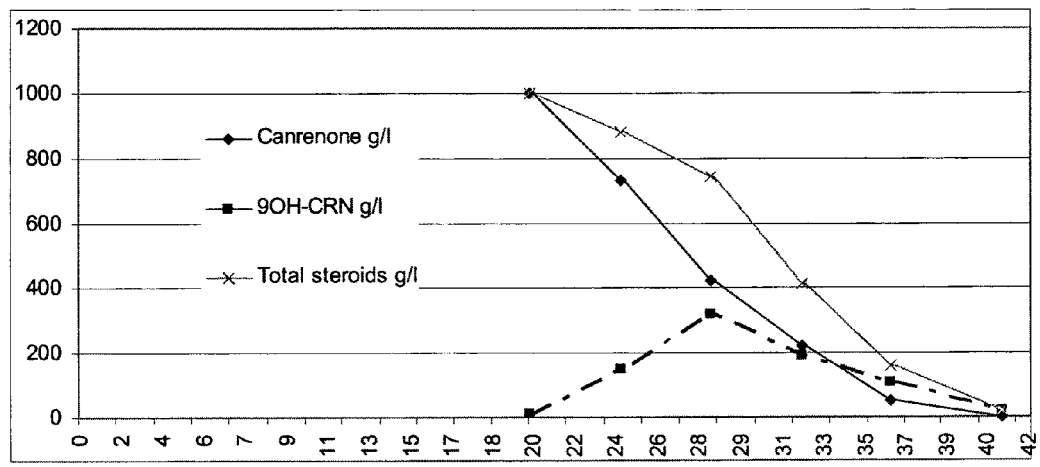
FIG. 1 is a graph, plotting time in hours against starting steroid, 9α-hydroxy steroid and total steroid concentrations in g/l that shows the characteristic steroid conversion pattern of the Nocardia sp. RG 1369 mother strain under the previously given fermentation conditions using canrenone substrate with degradation of the steroid skeleton.
Figure 2:
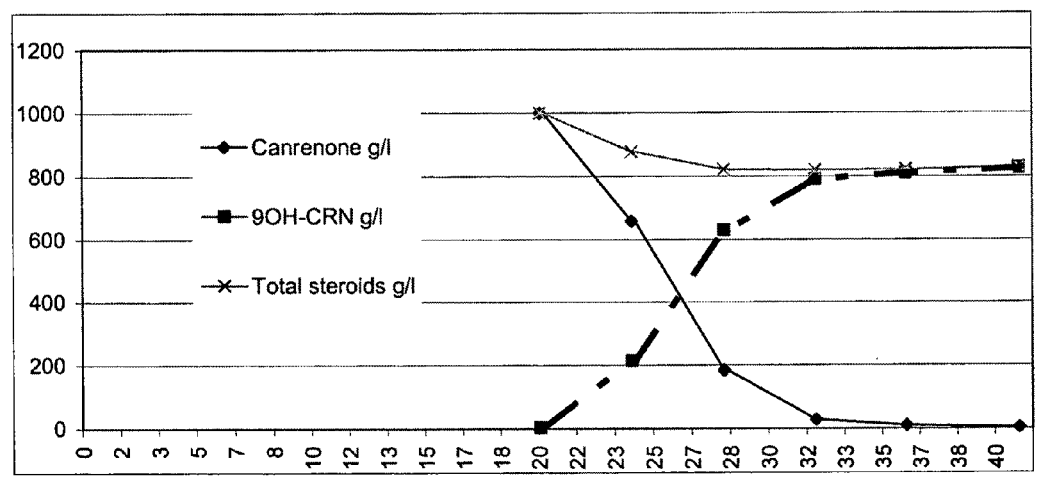
FIG. 2 is a graph, plotting time in hours against starting steroid, 9α-hydroxy steroid and total steroid concentrations in g/l shows the conversion ability of Nocardia farcinica NCAIM (P)—B 001342 strain under the same conditions, but without degradation of the steroid skeleton.

The invention is illustrated by the following not limiting examples.

EXAMPLE 1

The culture of *Nocardia farcinica* NCAIM (P)—B 001342 is maintained on the following agar slopes:

| Component | g/dm$^3$ |
|---|---|
| Potato dextrose agar | 39 |
| Agar-agar | 5 |
| Sterilization | at 121° C. for 20 min |

The inoculated culture was incubated at 32° C. for 4 days, then it was kept at +4-10° C. for further 30 days in order to initiate proliferation. Vegetative culture was made by transferring the suspension of the surface culture into 100 cm$^3$ of sterilized culture medium of the following composition in a 500 cm$^3$ flask:

| Component | g/dm$^3$ |
|---|---|
| Glycerol | 10 |
| Yeast extract | 1.5 |
| Malt extract | 5 |
| Ammonium chloride | 3 |
| Potassium dihydrogenphosphate | 0.5 |
| Magnesium sulfate heptahydrate | 0.5 |
| Iron(III)chloride hexahydrate | 0.05 |
| Calcium carbonate | 3 |
| Adjusting the pH: | to 6.7-6.8 with 20% NaOH solution |
| Sterilization: | at 121° C. for 30 min |

The culture was shaken at 32° C. for 48 h with 200 rpm, then 10% of it was used to inoculate 100 cm$^3$ of sterilized culture medium of the following composition in a 500 cm$^3$ flask:

| Component | g/dm$^3$ |
|---|---|
| Glycerol | 10 |
| Yeast extract | 1.5 |
| Malt extract | 5 |
| Ammonium chloride | 3 |
| Potassium dihydrogenphosphate | 0.5 |
| Magnesium sulfate heptahydrate | 0.5 |
| Iron(III)chloride hexahydrate | 0.05 |
| Calcium carbonate | 3 |
| Adjusting the pH: | to 6.7-6.8 with 20% NaOH solution |
| Sterilization: | at 121° C. for 30 min |

The culture was shaken at 32° C. for 72 h with 200 rpm, then 10% of it was used to inoculate 100 cm$^3$ of sterilized culture medium of the following composition in a 500 cm$^3$ flask:

| Component | g/dm$^3$ |
|---|---|
| Glycerol | 15 |
| Yeast extract | 5 |
| Malt extract | 5 |
| Soy flour | 5 |
| Adjusting the pH: | to 6.9-7.1 with 20% NaOH solution |
| Sterilization: | at 121° C. for 30 min |

The culture was shaken at 32° C. for 72 h with 200 rpm, then at the age of 18 h the formation of the 9α-hydroxylase enzyme was induced by adding 5 mg of 10,11-dihydroxylevodione dissolved in a 3:1 mixture of methanol-water. After 6 h induction 0.4 g of ketolactone substrate (chemical name: 17-hydroxy-3-oxo-17α-pregna-4-ene-21-carboxylic acid gamma lactone) dissolved in dimethyl formamide was added to the culture. After further 16 h the culture was extracted with chloroform, the organic layer was concentrated, the residue was recrystallized from ethyl acetate, filtered and dried. The so obtained crystalline material was 456 mg. According to HPLC measurement it contained 74.3% of the product, that is 339 mg (which means 84.7% yield) of 9α-hydroxy-ketolactone (chemical name: 9α,17-dihydroxy-3-oxo-17α-pregna-4-ene-21-carboxylic acid gamma lactone).

The so obtained product was characterized by NMR measurement. The typical chemical shifts are the following:

¹H NMR {500 MHz, DMSO-d$_6$(TMS), δ(ppm)}: 0.87 (3H, s, 18-Me); 1.20 & 1.67 (2H, m & m, H-12); 1.25 (3H, s, 19-Me); 1.32 & 1.54 (2H, m & m, H-15); 1.43 & 1.48 (2H, m & m, H-7); 1.47 & 1.67 (2H, m & m, H-11); 1.58 & 2.33 (2H, m & m, H-1); 1.65 (1H, m, H-9); 1.86 & 2.05 (2H, m & m, H-16); 1.90 (1H, m, H-8); 1.92 & 2.37 (2H, m & m, H-20); 2.17 & 2.38 (2H, m & m, H-2); 2.20 & 2.43 (2H, m & m, H-6); 2.40 & 2.54 (2H, m & m, H-21); 4.18 (1H, s, OH); 5.65 (1H, m, H-4)

¹³C NMR {125 MHz, DMSO-d$_6$(TMS), δ(ppm)}: 13.6 (C-18); 19.4 (C-19); 22.3 (C-15); 24.3 (C-7); 25.8 (C-11); 26.5 (C-12); 27.9 (C-1); 28.8 (C-21); 30.5 (C-20); 31.3 (C-6); 33.8 (C-2); 34.8 (C-16); 37.4 (C-8); 42.0 (C-14); 44.0 (C-10); 44.9 (C-13); 75.1 (C-9); 95.3 (C-17); 124.9 (C-4); 170.6 (C-5); 176.3 (C-22); 197.9 (C-3)

EXAMPLE 2

The experiment was carried out as described in Example 1, but the main phase culture was produced in a laboratory fermenter.

The inoculum culture was shaken at 32° C. for 72 h with 200 rpm, then the content of 5 flasks was used to inoculate 5 dm³ of sterilized main phase culture medium of the following composition into a 9 dm³ jar fermenter:

| Component | g/dm³ |
|---|---|
| Glycerol | 15 |
| Yeast extract | 5 |
| Malt extract | 5 |
| Soy flour | 5 |
| SB 2020 | 0.5 |
| Adjusting the pH: | to 6.9-7.1 with 20% NaOH solution |
| Sterilization: | at 121° C. for 30 min |

The culture was stirred at 32° C. for with 300 l/min speed and 200 dm³/h aeration rate. At the age of 18 h the formation of the 9α-hydroxylase enzyme was induced in the culture by adding 250 mg of 10,11-dihydroxy-levodione dissolved in a 3:1 mixture of methanol-water. After 6 h induction 5 g of canrenone substrate (chemical name: 17-hydroxy-3-oxo-17α-pregna-4,6-diene-21-carboxylic acid gamma lactone) dissolved in ethanol was added to the culture. The bioconversion was carried out in the same fermenter at 30° C., stirring with 300 l/min speed and 200 dm³/h aeration rate. After further 16 h the culture was extracted with chloroform, the organic layer was concentrated, the residue was recrystallized from ethyl acetate, filtered and dried. The so obtained crystalline material was 5.66 g. According to HPLC measurement it contained 72.4% of the product, that is 4.1 g (which means 82% yield) of 9α-hydroxy-kanrenon (chemical name: 9α,17-dihydroxy-3-oxo-17α-pregna-4,6-diene-21-carboxylic acid gamma lactone).

The so obtained product was characterized by NMR measurement. The typical chemical shifts are the following:

¹H NMR {500 MHz, DMSO-d$_6$(TMS), δ(ppm)}: 0.92 (3H, s, 18-Me); 1.15 (3H, s, 19-Me); 1.22 & 1.75 (2H, m & m, H-12); 1.48 & 1.67 (2H, m & m, H-11); 1.48 & 1.77 (2H, m & m, H-15); 1.64 & 2.25 (2H, m & m, H-1); 1.92 & 2.10 (2H, m & m, H-16); 1.94 & 2.36 (2H, m & m, H-20); 1.97 (1H, m, H-8); 2.26 & 2.54 (2H, m & m, H-2); 2.42 & 2.57 (2H, m & m, H-21); 2.50 (1H, m, H-9); 4.13 (1H, s, OH); 5.65 (1H, br, H-4); 5.89 (1H, dd, H-7); 6.18 (1H, dd, H-6)

¹³C NMR {125 MHz, DMSO-d$_6$(TMS), δ(ppm)}: 13.3 (C-18); 18.8 (C-19); 21.5 (C-15); 25.2 (C-11); 26.2 (C-12); 26.7 (C-1); 28.6 (C-21); 30.4 (C-20); 33.3 (C-2); 34.7 (C-16); 39.2 (C-8); 40.6 (C-14); 42.0 (C-10); 45.5 (C-13); 74.1 (C-9); 94.9 (C-17); 124.6 (C-4); 127.9 (C-6); 136.2 (C-7); 162.5 (C-5); 176.2 (C-22); 198.1 (C-3)

What we claim is:

1. A biologically pure culture of Nocardia farcinica strain NCAIM (P)—B 001342, capable of synthesising a compound of the Formula (I)

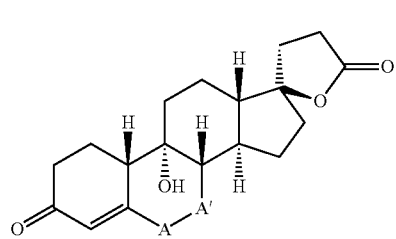

by 9-hydroxylation of a compound of the Formula (II)

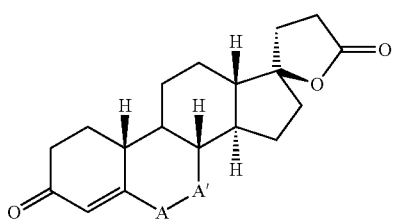

wherein in each of formula (I) and (II) -A-A'- is a —$CH_2$—$CH_2$— or —CH=CH— group.

2. A method for preparing the Nocardia farcinica NCAIM (P)—B 001342 culture of claim 1, the method comprising:
   (a) irradiating a culture containing a Nocardia sp. RG 1369 strain with mutagenic UV light having a wavelength of 254 nm for a period of time sufficient to magnetically transform the Nocardia sp. RG 1369 strain; and
   (b) isolating from the irradiated culture and biologically pure culture of Nocardia farcinica NCAIM (P)—B 001342.

3. The method of claim 2, wherein the *Nocardia* sp. RG 1369 culture is an aseptic culture suspended in physiological saline; and wherein the irradiating with the UV light comprises positioning a UV lamp 15 cm from the aseptic culture and irradiating the aseptic culture with UV light from the lamp for 23 minutes.

4. A process for the selective synthesis of a compound of the formula (I)

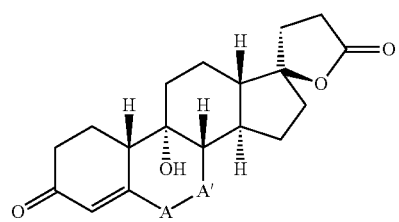

wherein -A-A'- is a —$CH_2$—$CH_2$— or —CH=CH— group, wherein the prose comprises the steps of:
   (a) bioconverting a compound of the formula: (II)

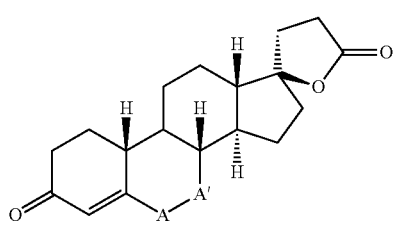

wherein -A-A'- is a —$CH_2$—$CH_2$— or —CH=CH— group, by hydroxylating the compound of the Formula (II) using an isolated Nocardia farcinica bacterium strain NCAIM (P)—B 001342; and
   (b) isolating the hydroxylated compound of the Formula (I) from the bioconverting step.

5. The process according to claim 4, wherein the bioconverting comprises obtaining more than 80% bio conversion of the compound of the Formula (II) to the compound of the Formula (I).

6. The process according to claim 4 wherein the compound of the Formula (I) is 9α,17-dihydroxy-3-oxo-17α-pregna-4-ene-21-carboxylic acid gamma lactone.

7. The process according to claim 4 wherein the compound of the Formula (I) is 9α,17-dihydroxy-3-oxo-17α-prena-4,6-diene-21-carboxylic acid gamma lactone.

* * * * *

UNITED STATES PATENT AND TRADEMARK OFFICE
CERTIFICATE OF CORRECTION

PATENT NO. : 8,367,394 B2  
APPLICATION NO. : 12/665351  
DATED : February 5, 2013  
INVENTOR(S) : Olasz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this
First Day of September, 2015

Michelle K. Lee
*Director of the United States Patent and Trademark Office*